US00PP15488P2

(12) United States Plant Patent
George

(10) Patent No.: US PP15,488 P2
(45) Date of Patent: Jan. 25, 2005

(54) NECTARINE TREE, 'GBN-ONE'

(50) Latin Name: ***Prunus persica* var. *nucipersica***
Varietal Denomination: GBN-One

(75) Inventor: Michael G. George, Dinuba, CA (US)

(73) Assignee: George Brothers, Inc., Sultana, CA (US)

( * ) Notice: Subject to any disclaimer, the term of this patent is extended or adjusted under 35 U.S.C. 154(b) by 4 days.

(21) Appl. No.: 10/699,004

(22) Filed: Oct. 30, 2003

(51) Int. Cl.[7] ..... A01H 5/00
(52) U.S. Cl. ..... Plt./190
(58) Field of Search ..... Plt./190

*Primary Examiner*—Bruce R. Campell
*Assistant Examiner*—S. B. McCormick-Ewoldt
(74) *Attorney, Agent, or Firm*—Wells St. John P.S.

(57) ABSTRACT

A new distinct variety of nectarine tree is disclosed, and which produces an attractively colored clingstone nectarine which is mature for harvesting and shipment approximately August 20–24$^{th}$ under the ecological conditions prevailing in the San Joaquin Valley of central California.

1 Drawing Sheet

BACKGROUND OF THE NEW VARIETY

The present invention relates to a new and distinct variety of nectarine tree, *Prunus persica* var. *nucipersica*, and which will hereinafter be denominated varietally as 'GBN-ONE,' and more particularly to a nectarine tree which produces fruit which are mature for harvesting and shipment during the third week of August in the central San Joaquin valley of California.

DISCOVERY AND ASEXUAL REPRODUCTION

The present variety of nectarine tree was discovered as a bud sport of the 'August Red' nectarine tree (U.S. Plant Pat. No. 6,363) during the 2000 growing season. The new variety was discovered in a cultivated nectarine orchard which is located along Avenue 400 and Road 120 near the town of Orosi, Calif. The inventor upon identifying the promising new variety asexually reproduced the newly discovered variety during the dormant season between the years of 2000 and 2001 by budding the newly discovered variety of nectarine tree onto 'Nemaguard' (unpatented) rootstock at an orchard which is located along Avenue 408 and Road 136 near Cutler, Calif. These asexually reproduced trees bore their first fruit during August, 2002. The inventor has carefully compared the asexually reproduced trees with that of the original bud sport including the fruit produced by the respective trees. Still further, it was confirmed during the 2003 growing season that the trees and fruit produced by these asexual reproductions are identical in all respects to the original bud sport.

SUMMARY OF THE VARIETY

The 'GBN-ONE' nectarine tree is characterized principally as to novelty by producing a clingstone fruit having an exceptionally desirable coloration, and which matures during the third week of August under the climatic conditions prevailing in the central San Joaquin Valley. This date of harvesting is about 3 to 5 days after the 'August Fire' nectarine tree (U.S. Plant Pat. No. 11,477) which also produces a highly colored fruit, and is further closely similar in its harvesting date to the 'August Red' nectarine tree (U.S. Plant Pat. No. 6,363), from which it was derived from a bud sport. However, the present variety is clearly distinguishable from the 'August Red' nectarine tree (U.S. Plant Pat. No. 6,363) by producing a more highly colored nectarine fruit. The present variety 'GBN-ONE' is also noted for its good flavor, noteworthy storage characteristics and further that the fruit holds well on the tree prior to harvest. The asexually reproduced trees appear to bear consistently from year to year.

BRIEF DESCRIPTION OF THE DRAWINGS

The accompanying drawing is a color photograph showing a characteristic twig bearing typical leaves; several leaves showing both the dorsal and ventral coloration thereof, and several mature fruit showing their external coloration when sufficiently matured for harvesting and shipment. Additionally, a single stone is shown along with two fruit of the subject variety which have been dissected and which illustrate the flesh and stone characteristics of the newly discovered variety.

DETAILED DESCRIPTION

Referring more specifically to the horticultural details of this new and distinct variety of nectarine tree, the following characteristics have been observed under the ecological conditions prevailing at the orchard of origin which is located near Orosi, Calif. in the San Joaquin Valley of central California. All major color code designations are by reference to the Dictionary of Color by Maerz and Paul, 1$^{st}$ Ed. 1930. Common color names are also occasionally employed.

TREE

Size: Medium for the variety. The present asexually reproduced trees have not reached full size as of the date of this application. These third leaf trees presently are about 4–6 feet high and have a spread of about 3–4 feet.

Vigor: Considered good.

Chilling requirement: Appears average for nectarine trees cultivated in the central San Joaquin Valley of California.

Figure: Upright and slightly spreading in its tropism.

Productivity: Considered very good for a tree in its third year of production (third leaf).

Regularity of bearing: Considered regular.

TRUNK

Size: Generally — Large, relatively speaking, for a third leaf tree, about 10 inches in circumference when measured at a distance of about 12 inches above the soil surface.
Surface texture: Considered rough.
Bark color: Brown, Plate 55-E-2.
Lenticels: Generally, numerous, moderately sized lenticels are observed.

BRANCHES

Size: Generally speaking, the branches are medium to large for a third leaf tree.
Average circumference: About 6 inches.
Crotch angle of the branches: About 48 degrees. This is not particularly distinctive of the new variety, however.
Surface texture: Mature wood — Considered slightly rough.
Surface texture: Immature wood — Considered glabrous.
Bark color: One year or older wood — Light brown, Plate 6-C-9.
Bark color: Immature wood — Green, Plate 20-K-5.
Lenticels: Numbers — Few, approximately 10–15 lenticels are located between the internodes.
Lenticels: Size — Considered small, about 1–2 mm in length, and having a color of mauve castor, plate 55-H-2.

LEAVES

Size: Generally — Considered large for the species.
Leaf length: About 155 to about 172 millimeters (6.10 to about 6.77 inches).
Leaf width: About 41 to about 45 millimeters (1.61 to about 1.77 inches).
Leaf shape: Considered lanceolate.
Leaf color: Upwardly disposed surface, dark green, Plate 23-J-9.
Leaf color: Downwardly disposed surface, light green, Plate 20-K-6.
Marginal form: Considered serrate.
Leaf vein color: Light green, Plate 20-L-3.
Leaf vein: Thickness — About 2 millimeters, (0.079 inches).
Leaf glandular characteristics: Generally speaking approximately 3 to 4 reniform shaped glands may be observed on the stem.
Petiole: Size — Medium for the species.
Petiole length: About 10 to 12 millimeters (0.39 to about 0.47 inches).
Petiole thickness: About 2 millimeters (0.079 inches).
Petiole color: Light green, Plate 20-K-6.

FLOWERS

Flower bud: Size — Generally considered average for the species.
Flower bud length: About 8 millimeters (0.314 inches).
Flower bud width: About 8 to about 10 millimeters (0.314 to about 0.394 inches).
Flower bud surface texture: Slightly pubescent.
Flowers: Generally — The flowers are considered to be a showy type. The present flowers are considered perfect flowers, and no additional pollination is required to set fruit.
Flower position: The flowers are normally located on opposite locations on the twigs.
Flowers: Fragrance — Considered highly fragrant.
Date of first bloom: This was first observed on February 26$^{th}$. The first bloom was in a range of about 50% to about 75% on that date.
Size of flowers: Medium, about 25 to about 28 millimeters (0.98 to about 1.10 inches) in diameter.
Flower petals: Length — About 13 millimeters (0.51 inches).
Flower petal width: About 8 millimeters (0.314 inches).
Flower petal color: Generally considered light pink. Although the region in the middle of the flower petal on its downwardly facing surface is considered white, Plate 1-B-1.
Petal margin color: A darker pink, Plate 1-D-3.
Petal claws: Shape — Considered broadly truncate and small for the variety.
Petal claw: Width — Less than about 1 millimeter.
Petal claw: Length — Less than about 1 millimeter.
Petal margin: Shape — Considered moderately undulate and having a rounded apex.
Pedicels: Length — Considered very short, approximately 4 millimeters, (0.158 inches).
Pedicels: Width — About 2 millimeters, (0.079 inches).
Calyx surface texture: Considered slightly pubescent.
Calyx: Color — Maroon, Plate 7-L-7.
Sepals: Numbers — 5. The sepals are slightly pubescent.
Sepals: Size — About 4 to about 5 millimeters in width, (0.158 to about 0.197 inches), and about 6 millimeters (0.24 inches) in length.
Anthers: Size — Considered very small and less than about 1 millimeter in length.
Anthers: Color — Brown, Plate 14-L-12.
Stamens: Numbers — Numerous, between 26–32 may be observed.
Stamens: Length — About 6 to about 10 millimeters (0.24 to about 0.39 inches).
Filament color: Red, Plate 6-F-5.
Pistil: Length — About 16 to about 18 millimeters (0.63 to about 0.71 inches).
Pistil: Color — The pistil has a light green colored base, approximately Plate 20-J-3. Further, a rose colored region near the apex may be observed.

FRUIT

Date of maturity when described: The present variety of nectarine tree is described hereinafter as it would be observed bearing ripe fruit at full commercial maturity. In this regard, the fruit of the present variety was picked during August 20–24. These dates of harvesting were observed under the ecological conditions prevailing in the San Joaquin Valley of central California. This date of harvesting is approximately 3–5 days after the 'August Fire' nectarine tree (U.S. Plant Pat. No. 11,477) at the same geographical location.
Size: Generally — Average and considered uniform. Based upon the present fruit size, the average weight of the fruit ranges from about 6 to about 8 ounces. This weight range is not considered a characteristic of the present variety because it may be readily altered by cultural practices, that is, thinning, irrigation, fertilization, and pruning, as well as unseasonal environmental conditions.
Average axial diameter: Approximately 65 to about 70 millimeters (about 2.56 to about 2.76 inches).
Average diameter (transverse in the suture plane): About 65 to about 70 millimeters (2.56 to about 2.76 inches).
Average diameter (transverse at right angles to the suture plane): About 71 to about 74 millimeters (2.80 to about 2.91 inches).

Fruit form: Considered nearly uniform and having a slight nipple. Still further the fruit is nearly symmetrical and is noteworthy in having a smooth ventral surface.
Stem cavity: Width — About 15 to about 25 millimeters (0.59 to about 0.98 inches).
Stem cavity: Depth — About 19 to about 28 millimeters, (0.78 to about 1.10 inches).
Stem cavity: Length — About 22 to about 30 millimeters, (0.87 to about 1.18 inches).
Stem cavity: Shape — Ovate.
Stem: Length — Considered short, about 3 to about 4 millimeters (0.12 to about 0.16 inches).
Stem: Caliper — About 4 millimeters, (0.16 inches).
Apex: Shape — Rounded.
Pistil point: Present and considered prominent.
Fruit skin: Thickness — Considered average for nectarines.
Skin texture: Considered smooth and firm.
Tendency to crack: Not observed.
Skin color: Blush — Dark purple, Plate 54-L-12. This variety is considered highly colored when compared with 'August Red' nectarine (U.S. Plant Pat. No. 6,363), from which it was derived as a bud sport.
Ground color: Yellow-Orange, Plate 9-K-6.
Flesh color: Green-orange, Plate 12-L-4.
Color of surface cavity: Dark purple, Plate 52-L-8.
Color of pit well: Reddish purple, Plate 53-L-6.
Juice production: Considered good.
Flavor: Considered to be very good.
Aroma: Pleasing.
Texture: Firm, considered semi-hard at full commercial maturity.
Fibers: Many are observed. The observed fibers have a stringy texture.
Ripening: Considered even.
Eating quality: Considered very good.

STONE

Attachment: Considered a clingstone at full commercial maturity.
Fibers: Numbers — Many.
Fibers: Length — About 12 to about 15 millimeters (0.47 to about 0.59 inches).
Stone size: Generally considered large.
Stone: Length — About 34 to about 40 millimeters (1.34 to about 1.57 inches).
Stone: Width — About 24 to about 28 millimeters (0.94 to about 1.10 inches).
Stone: Thickness — About 19 to about 20 millimeters (0.75 to about 0.79 inches).
Stone form: Ovate.
Stone apex: Shape — Slightly rounded and having a slight point.
Stone: Dry color — Purple, Plate 54-J-6, to about Plate 55-L-8.
Base: Shape — Somewhat flattened.
Sides: Shape — Considered uneven.
Ridges: Generally — The stone surface is heavily ridged. The ridges appearing on the ventral edge are narrower than those appearing elsewhere.
Tendency to split: Occasional split pits have been found.
Fruit use: The present variety is considered to be a fresh market nectarine for both local and long distance markets.
Keeping quality: Considered very good.
Resistances to disease: No readily apparent susceptibilities have been noted during the observation period.

Although the new variety of nectarine tree possesses the desired characteristics when grown under the ecological conditions prevailing near the orchard of origin, in the central part of the San Joaquin Valley of California, it should be understood that variations of the usual magnitude and characteristics incident to changes in growing conditions, fertilization, pruning, and pest control as well as horticultural management practices are to be expected.

Having thus described and illustrated my new variety of nectarine tree, what I claim is new and desire to secure by Plant Letters Patent is:

1. A new distinct variety of nectarine tree as substantially shown and described and which is characterized principally as to novelty by producing an attractively colored clingstone nectarine which is mature for harvesting and shipment approximately August 20–24$^{th}$ under the ecological conditions prevailing in the San Joaquin Valley of central California.

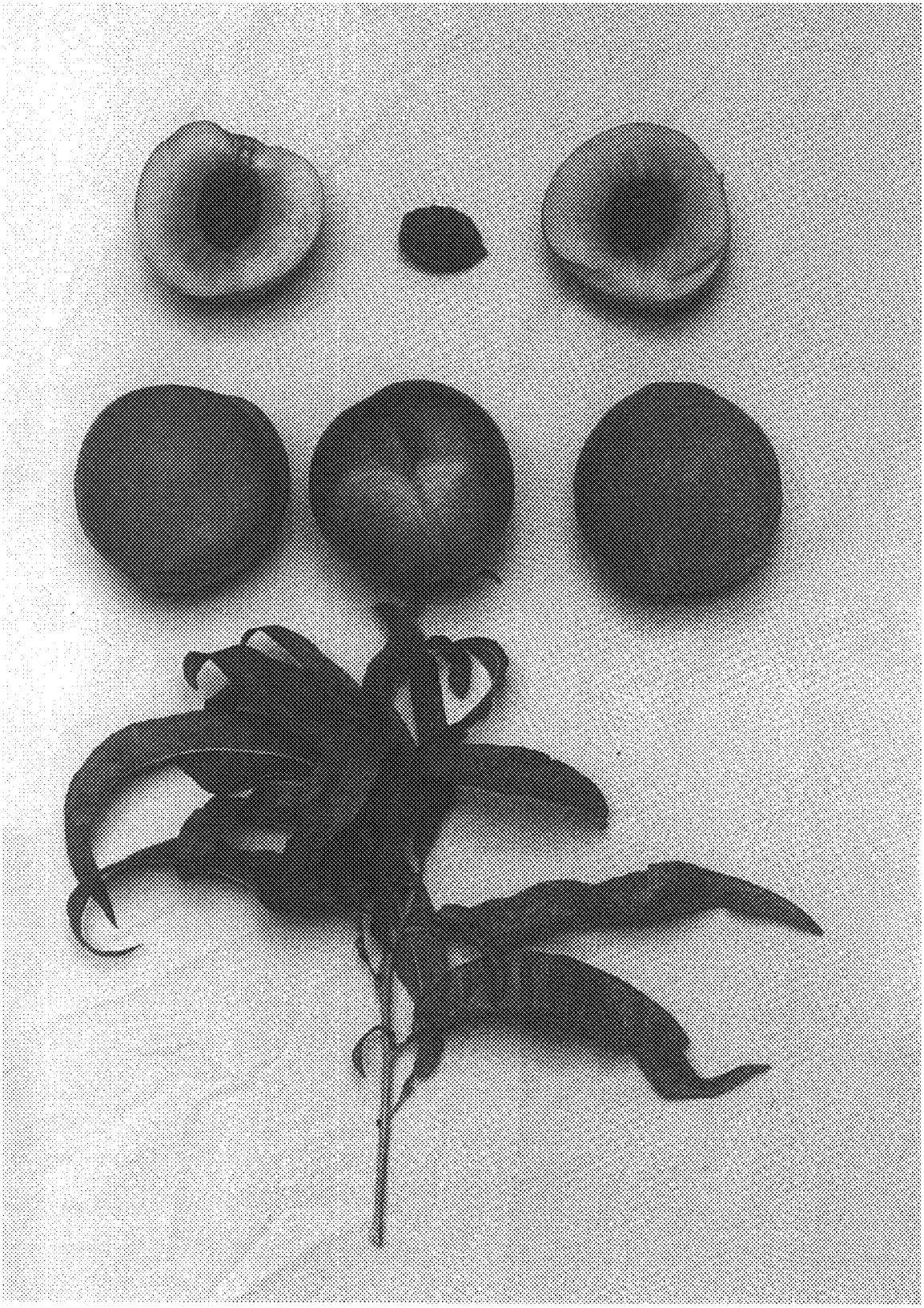

* * * * *